(12) United States Patent
Natsch et al.

(10) Patent No.: US 9,198,845 B2
(45) Date of Patent: Dec. 1, 2015

(54) GLUTAMINE DERIVATIVES AS DEODORANTS

(75) Inventors: Andreas Natsch, Uetikon (CH); Thierry Granier, Duebendorf (CH)

(73) Assignee: Givaudan S.A., Vernier (CH)

( * ) Notice: Subject to any disclaimer, the term of this patent is extended or adjusted under 35 U.S.C. 154(b) by 268 days.

(21) Appl. No.: 13/880,998

(22) PCT Filed: Oct. 28, 2011

(86) PCT No.: PCT/EP2011/069020
§ 371 (c)(1),
(2), (4) Date: May 20, 2013

(87) PCT Pub. No.: WO2012/056014
PCT Pub. Date: May 3, 2012

(65) Prior Publication Data
US 2014/0147403 A1    May 29, 2014

(30) Foreign Application Priority Data

Oct. 28, 2010 (GB) .................................. 1018171.7

(51) Int. Cl.
| | |
|---|---|
| *A61K 8/42* | (2006.01) |
| *A61Q 15/00* | (2006.01) |
| *A61K 8/44* | (2006.01) |
| *C07C 275/16* | (2006.01) |
| *C07C 275/24* | (2006.01) |
| *C07C 275/28* | (2006.01) |

(52) U.S. Cl.
CPC ... *A61K 8/42* (2013.01); *A61K 8/44* (2013.01); *A61Q 15/00* (2013.01); *C07C 275/16* (2013.01); *C07C 275/24* (2013.01); *C07C 275/28* (2013.01)

(58) Field of Classification Search
None
See application file for complete search history.

(56) References Cited

U.S. PATENT DOCUMENTS

| | | |
|---|---|---|
| 5,463,063 A | 10/1995 | Muller |
| 5,554,588 A | 9/1996 | Behan et al. |
| 5,643,559 A | 7/1997 | Eigen et al. |
| 5,698,579 A | 12/1997 | Muller |
| 5,800,804 A | 9/1998 | Laney |
| 5,925,339 A | 7/1999 | Acuna et al. |
| 5,942,217 A | 8/1999 | Woo et al. |
| 6,528,499 B1 * | 3/2003 | Kozikowski et al. ............ 514/75 |
| 2004/0052826 A1 * | 3/2004 | Fernandez-Kleinlein et al. ............................ 424/401 |
| 2005/0042182 A1 * | 2/2005 | Arkin et al. ..................... 424/47 |
| 2008/0014393 A1 | 1/2008 | Denome et al. |

FOREIGN PATENT DOCUMENTS

| | | |
|---|---|---|
| EP | 0207358 A2 | 1/1987 |
| EP | 0545556 A2 | 6/1993 |
| EP | 0 815 833 A2 | 1/1998 |
| EP | 1 258 531 A1 | 11/2002 |
| WO | WO 91/05541 A1 | 5/1991 |
| WO | WO 95/01348 A1 | 1/1995 |
| WO | WO 01/88076 A1 | 11/2001 |
| WO | WO 2004/043971 A1 | 5/2004 |
| WO | WO 2012/101241 A1 | 8/2012 |

OTHER PUBLICATIONS

Johnston et al. Journal of Medicinal Chemistry, 9, p. 892-911, 1966.*
Wang et al. Bioorganic & Medicinal Chemistry Letters, 20, p. 392-397, 2010.*
PCT/EP2011/069020—International Search Report, Dec. 12, 2011.
PCT/EP2011/069020—International Written Opinion, Dec. 12, 2011.
PCT/EP2011/069020—International Preliminary Report on Patentability, Apr. 30, 2013.
GB 1018171.7—Search Report, Jan. 19, 2011.
Gaunt, et al., "The Action of Phenyl Isocyanate on Insulin. II. Further Observations on the Chemistry of Insulin and its Phosphate Lowering Power", Biochemical Journal, The Biochemical Society, Jan. 1, 1936; vol. 30, pp. 1915-1922; London, England.

* cited by examiner

*Primary Examiner* — Nissa Westerberg
(74) *Attorney, Agent, or Firm* — Curatolo Sidoti Co., LPA; Joseph G. Curatolo; Salvatore A. Sidoti

(57) ABSTRACT

Compounds of the formula (I)

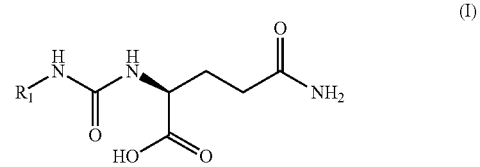

or salts thereof, wherein $R_1$ represents alkyl, aryl, alkyl-aryl or aryl-alkyl, compositions containing same, and their use in counteracting human axillary malodour.

12 Claims, No Drawings

GLUTAMINE DERIVATIVES AS DEODORANTS

CROSS REFERENCE TO RELATED APPLICATIONS

This application is a national stage application of International Application No. PCT/EP2011/069020, filed 28 Oct. 2011, which claims priority from Great Britain Patent Application No. 1018171.7, filed 28 Oct. 2010, from which applications priority is claimed, and which are incorporated herein by reference.

The present invention is concerned with novel compounds that are useful in the prevention or reduction of human malodour, in particular human axillary malodour, and with compositions containing same.

Human skin is covered with sweat glands and the axilla regions of humans contains a particularly dense arrangement of them. Volatile substances evaporating from this area of the human body make a key contribution to human body malodour.

The sweat secreted from axillary glands is odourless. It is now appreciated that the action of bacteria colonising the skin is needed to generate the odoriferous principles from the non-odorous sweat. The axilla is a region of the skin that is populated densely with bacteria. This bacterial population is generally dominated by two genera, namely *Staphylococcus* and *Corynebacteria*. Strong axillary malodour has been correlated with the presence of a high population of the latter.

It is known that fresh sweat contains odourless precursor molecules, which are transformed into foul-smelling volatile substances by enzymes contained in *Corynebacteria*. More specifically, it is known that N alpha acyl glutamine substrates represent the main precursors contained in sweat and they are cleaved by the enzyme N alpha acyl glutamine aminoacylase expressed by *Corynebacteria* to release unpleasant-smelling fatty acids.

It has been proposed to eliminate or at least ameliorate malodour by inhibiting this bacterial enzyme such that it can no longer act on these non-odoriferous precursors.

U.S. Pat. No. 5,925,339 discloses a class of glutamine derivatives as fragrance precursors for preventing human malodour. It was not appreciated that these glutamine derivatives acted on an enzyme and indeed the particular enzyme N alpha acyl glutamine aminoacylase was not even known at the date of filing this citation.

In fact, glutamine derivatives described in this patent that are competitive substrates of the enzyme N alpha acyl glutamine aminoacylase. That is, when these derivatives are brought into contact with the enzyme, they are cleaved by it.

These competitive substrates compete with the N alpha acyl glutamine substrates contained in sweat for the enzyme. Naturally, as the competitive substrates bind to the enzyme and are cleaved, their concentration falls as a function of time. As the concentration of these competitive substrates falls, they are unable to compete as effectively with the N alpha acyl glutamine substrates and the malodour counteracting activity of a deodorant composition containing the competitive substrates also diminishes. Accordingly, if a prolonged malodour counteracting effect is required, high concentrations of these competitive substrates must be employed in underarm deodorant compositions to account for these attritional effects.

There remains a need to provide compounds that are inhibitors of the enzyme N alpha acyl glutamine aminoacylase expressed by bacteria, in the sense that they bind to the enzyme and interfere with the enzyme function and are not merely competing substrates that are consumed by the enzyme. Only in this way can highly potent malodour counteracting active agents be developed, which are capable of exerting extended duration of deodorancy effects, even when employed in relatively low concentrations.

The applicant has surprisingly now found a group of glutamine derivatives that are not cleaved by enzyme N alpha acyl glutamine aminoacylase but which are truly inhibitors of the enzyme.

The invention provides in a first aspect a compound of the formula (I)

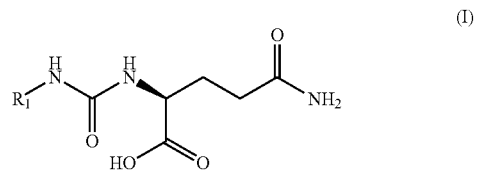

and salts thereof, wherein, $R_1$ represents alkyl, aryl, alkyl-aryl or aryl-alkyl, with the proviso that $R_1$ is not phenyl or naphthyl.

More particularly, $R_1$ represents 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, cyclooctyl, 5-phenyl-3-methyl-pentyl.

Particular compounds of formula (I) include

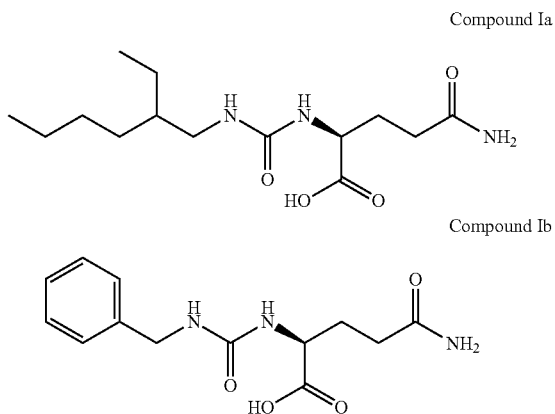

and salts thereof.

Compounds of formula (I) or their salts bind to the enzyme. This is the most important factor governing the efficacy of said compounds. Also important for activity is the ability of a compound to be taken up by the bacteria. We have surprisingly found that Compound Ia and Compound Ib exhibit particularly good efficacy as inhibitors and it is believed, without intending to be bound by any particular theory that these compounds are particularly well taken up by the bacteria.

The bacterial population on the human skin is of a high diversity, and a large number of species of *Corynebacteria* were reported. These bacteria possess differing aminoacylase enzymes, which may bind synthetic inhibitors with different affinity, but all of these aminoacylase enzymes have the commonality that they are able to cleave the natural substrate. Hence, inhibitors with a high structural similarity to the natural substrate, but which are not cleaved by the enzyme, may bind to the active site of the enzymes of a large number of bacterial species and thereby inhibit malodour formation from a wide spectrum of bacteria.

Compounds of formula (I) may be prepared according to known synthetic procedures, using commonly available starting materials. These methods and materials are known in the chemical literature.

Compounds of formula (I) are most conveniently prepared by addition of L-glutamine to alkyl or aryl isocyanates

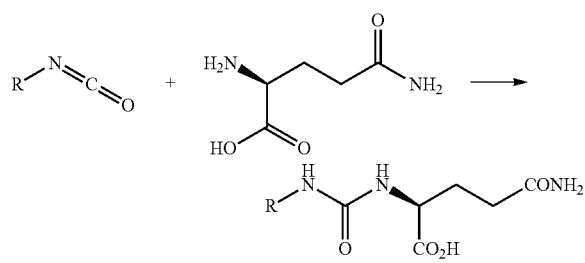

wherein, $R_1$ is as hereinabove defined.

The conditions under which this synthesis takes place are well known to the skilled person in the art and a general discussion here is not warranted. Further discussion of synthetic conditions is set out in the Examples, below.

The compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may be used to prevent, suppress or attenuate undesirable odours, particularly human malodour, more particularly human axillary malodour, when applied to the human skin, in particular, the skin in the axilla region.

The compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may be employed in consumer products such as cosmetic products primarily for use on human skin, such as under-arm deodorants, anti-perspirants or any other products for use on the skin. Consumer products may also include lotions, powders, ointments, body-wipes, colognes, shaving creams and the like.

The compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may also be employed in consumer products for treatment of fabrics, which then come into contact with the human skin. Preferably they are used in fabric enhancer products such as pre-wash or post-wash aerosols, trigger sprays, bars, non woven sheets, and liquid or granular fabric enhancers.

The compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may also be added to any laundry detergent and fabric softener product in order to be deposited on the fabric and then excert their activity once the fabric comes into contact with the human skin.

The compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, as stated already herein, are true inhibitors of the N alpha acyl glutamine aminoacyclase enzyme. As they are not cleaved, and therefore not consumed by the enzyme, they can be employed in rather lower concentrations in consumer products than would be possible if the compounds were merely competitive substrates cleavable by the enzyme.

Typically, compounds of the formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may be employed in consumer products in amounts ranging from 0.05-2%, preferably 0.1-1%.

In the preparation of a consumer product, the compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, may be combined with other ingredients used in consumer products used primarily in body deodorancy. An additional malodour-counteracting active agent may be desirable. This might be a perfume, an antiperspirant active, or an anti-microbial active.

Typical antiperspirant actives include astringent active salts, in particular, aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates. Levels of incorporation may be from 0.5% to 60%, by weight of the composition of which they form a part.

Typical anti-microbial actives include quaternary ammonium compounds (like cetyltrimethylammonium salts), chlorhexidine and salts thereof; diglycerol monocaprate, diglycerol monolaurate, glycerol monolaurate, polyhexamethylene biguanide salts (also known as polyaminopropyl biguanide salts—an example being Cosmocil CQ available from Arch chemicals), 2,4,4'-trichloro, 2'-hydroxy-diphenyl ether (triclosan), and 3,7,11-trimethyldodeca-2,6,10-trienol (farnesol). Levels of incorporation may be from 0.01% to 1% by weight of the composition.

Preferred antimicrobial actives are polyaminopropyl biguanide salts, which exhibit a particularly good efficacy if combined with compounds according this invention.

A salt of the compounds of formula (I) wherein $R_1$ represents alkyl, aryl, alkyl-aryl or aryl-alkyl, and more particularly 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, naphthyl, cyclooctyl, or 5-phenyl-3-methyl-pentyl, with polyaminopropyl biguanide may be formed and used directly in consumer products thereby providing both the antibacterial effect and the enzyme inhibition effect.

The consumer product may contain a carrier material that may be hydrophobic or hydrophilic, solid or liquid.

Hydrophobic liquids include liquid silicones, that is, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic liquids may be used. Such materials include mineral oils, hydrogenated polyisobutene, polydecene, paraffins, isoparaffins of at least 10 carbon atoms, aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers.

Hydrophilic liquid carrier materials, for example water, may also be employed.

Liquid carrier materials include organic solvents. They include organic solvents that are aliphatic alcohols, for example monohydric or polyhydric alcohols having 2 to 8 carbon atoms, and polyglycol ethers, such as oligoglycol ethers having 2 to 5 repeat units. Examples include dipropylene glycol, glycerol, propylene glycol, butylene glycol, ethanol, propanol, isopropanol, and industrial methylated spirits.

Mixtures of carrier materials may also be used. The amount of carrier material employed is preferably at least 5%, more preferably from 30% to 99% by weight of a consumer product composition.

Structurants and emulsifiers may also be employed in consumer product compositions of the invention. They may be present at levels from 1% to 30% by weight of the composition. Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers include steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants are perfume solubilisers and wash-off agents. Examples of the former include PEG-hydrogenated castor oil, available from BASF in the Cremaphor RH and CO ranges. Examples of the latter include poly(oxyethylene) ethers. Certain sensory modifiers are further desirable components in the compositions of the invention. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), polyethylene (eg. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in a consumer product composition of the invention. Suitable materials include conventional perfumes, such as perfume oils and also include so-called deo-perfumes, as described in EP 545,556 and other publications. These latter materials may also qualify as aditional organic anti-microbial agents. Levels of incorporation are preferably up to 4% by weight.

Further additional components that may also be included are colourants and preservatives, for example $C_1$-$C_3$ alkyl parabens.

If the consumer product composition is in the form of an aerosol composition, a volatile propellant is typically employed. The level of incorporation of the volatile propellant is typically from 30 to 99 parts by weight. Non-chlorinated volatile propellant are preferred, in particular liquefied hydrocarbons or halogenated hydrocarbon gases (particularly fluorinated hydrocarbons such as 1,1-difluoroethane and/or 1-trifluoro-2-fluoroethane) that have a boiling point of below 10.degrees Centigrade and especially those with a boiling point below zero degrees Centigrade. It is especially preferred to employ liquefied hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

The invention is further illustrated by the following examples.

EXAMPLE 1

Preparation of a Compounds of the Formula (I)

EXAMPLE 1a

N2-[(2-ethylhexylamino)carbonyl]-L-glutamine (Compound Ia)

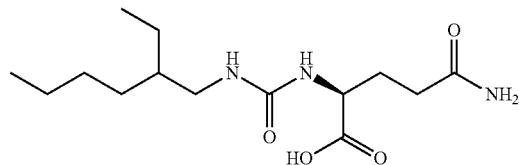 [SMILES: CCCCC(CC)CNC(=O)N[C@@H](CCC(N)=O)C(=O)O]

At 5° C., a suspension of L-(+)-glutamine (23.1 g, 158 mmol) in 1:1 water/dioxane (300 ml) was treated successively with a solution of 2N aq. NaOH (79 ml) and with 2-ethylhexyl isocyanate (25 g, 158 mmol). The resulting mixture was stirred for 24 h while its temperature rose to 20° C. (final pH value: 6) and filtered. The filtrate was washed twice with ethyl acetate (200 ml) and the combined organic phases were acidify with a 2N aq. HCl solution to pH 1. Filtration of the resulting precipitate and drying under vacuum gave N2-[(2-ethylhexylamino)carbonyl]-L-glutamine (42 g, 88%, white solid).

$^1$H-NMR (400 MHz, $(CD_3)_2SO$): δ7.60-7.10 (br. s, NH), 7.00-6.60 (br. s, NH), 6.50-5.80 (br. s, 2 H, $NH_2$), 4.06 (dd, J=5.1, 8.1, CHN), 2.99-2.86 (m, 2 H, $CH_2N$), 2.17-2.02 (m, 2 H, $CH_2CON$), 1.94-1.82 (m, 1 H), 1.75-1.62 (m, 1 H), 1.36-1.11 (m, 9 H), 0.86 (t, J=7.0, Me), 0.82 (t, J=7.3, Me).

$^{13}$C-NMR (100 MHz, $(CD_3)_2SO$): δ174.90 (s), 174.07 (s), 158.36 (s), 52.51 (d), 42.22 (t), 39.82 (d), 31.68 (t), 30.84 (t), 28.84 (t), 28.57 (t), 24.05 (t), 22.96 (t), 14.39 (q), 11.21 (q).

MS (EI): 285 (2), 284 (9), 283 (25), 267 (18), 266 (100), 265 (7), 237 (6), 225 (13), 210 (5), 194 (2), 185 (54), 172 (32), 168 (60), 155 (70), 154 (18), 140 (11), 129 (17), 127 (14), 126 (11), 113 (21), 84 (47).

EXAMPLE 1b

N2-[(benzylamino)carbonyl]-L-glutamine (Compound Ib)

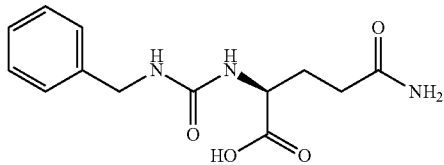 [SMILES: NC(=O)CC[C@H](NC(=O)NCc1ccccc1)C(=O)O]

Preparation from L-(+)-glutamine (5.39 g, 36.9 mmol) and benzyl isocyanate (4.96 g, 36.9 mmol) (final pH value after 24 h stirring: 8-9) gave N2-[(benzylamino)carbonyl]-L-glutamine (7.0 g, 68%, white solid).

$^1$H-NMR (400 MHz, $(CD_3)_2SO$): δ7.42-7.30 (br. s, NH), 7.34-7.18 (m, $C_6H_5$), 6.84-6.69 (br. s, NH), 6.74-6.48 (br. s, NH), 6.54-6.18 (br. s, NH), 4.24 (d, J=15.4, PhCHN), 4.19 (d, J=15.4, PhCHN), 4.10 (dd, J=5.2, 8.2, CHN), 2.19-2.05 (m, 2 H, $CH_2CON$), 1.97-1.86 (m, 1 H), 1.78-1.66 (m, 1 H).

$^{13}$C-NMR (100 MHz, $(CD_3)_2SO$): δ174.87 (s), 173.98 (s), 158.27 (s), 141.10 (s), 128.64 (d, 2C), 127.41 (d, 2C), 126.99 (d), 52.68 (d), 43.24 (t), 31.75 (t), 28.38 (t).

MS (EI): 262 (10), 261 (41), 245 (15), 244 (100), 216 (7), 203 (13), 202 (35), 188 (29), 173 (4), 153 (6), 138 (2), 132 (15), 129 (9), 125 (7), 106 (41), 91 (50).

EXAMPLE 1c

N2-[(3-benzylphenylamino)carbonyl]-L-glutamine

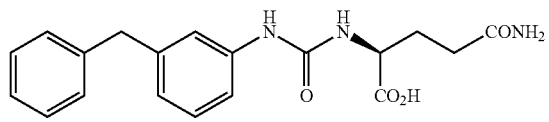 [SMILES: NC(=O)CC[C@H](NC(=O)Nc1cccc(Cc2ccccc2)c1)C(=O)O]

Preparation from L-(+)-glutamine (0.487 g, 3.33 mmol) and 3-benzylphenyl isocyanate (0.719 g, 3.33 mmol) (final pH value after 24 h stirring: 5-6) gave N2-[(3-benzylphenylamino)carbonyl]-L-glutamine (0.862 g, 73%, white solid).

$^1$H-NMR (400MHz, $(CD_3)_2SO$): δ 15.00-10.00 (br. s, $CO_2H$), 8.76-8.67 (br. s, NH), 7.48-7.04 (m, 9 H), 6.78 (br. s, NH), 6.77 (br. s, NH), 6.51 (br. d, J=7.1, NH), 4.20-4.09 (br. m, CHN), 3.86 (s, $PhCH_2$), 2.23-2.05 (m, 2H, $CH_2CON$), 2.04-1.91 (m, 1 H), 1.84-1.68 (m, 1 H).

$^{13}$C-NMR (100 MHz, $(CD_3)_2SO$): δ174.52 (s), 173.86 (s), 155.29 (s), 142.16 (s), 141.66 (s), 140.79 (s), 129.15 (d), 129.12 (d, 2C), 128.82 (d, 2C), 126.37 (d), 122.17 (d), 118.27 (d), 115.76 (d), 52.35 (d), 41.70 (t), 31.60 (t), 28.22 (t).

MS (EI): 338 (15), 337 (53), 321 (12), 320 (58), 279 (12), 278 (36), 226 (10), 210 (17), 209 (100), 208 (17), 201 (12), 184 (14), 183 (98), 182 (47), 181 (12), 180 (53), 167 (44), 165 (42), 152 (13), 91 (18).

EXAMPLE 2

Inhibition of Formation of Malodorous Acids: Comparison of Inventive Compound with Alternative Substrate

*Corynebacterium* Ax 20 was grown overnight, harvested and resuspended in a phosphate buffer (50 mM, pH 7.5). Different compounds were dissolved in dimethylsulfoxide and added to the cells at a final concentration of 10 ppm, 100 ppm 500 ppm and 1000 ppm. The cells were then preincubated with the test agent for 30 min, 4 h, 8 h or 24 h. After this pre-incubation period, the natural substrate Nα-(3-hydroxy-3-methyl-hexanoyl)-glutamine was added (1 mM final concentration) and the cells were further incubated for 90 min. The released 3-hydroxy-3-methyl-hexanoic acid was determined by GC-analysis and compared to control samples to assess the in vivo malodor reducing capacity of a given compound in the bacterial cells. The samples were then further analysed to determine the cleavage of the synthetic compound by the action of the bacterial enzymes.

Inventive Compound Ia

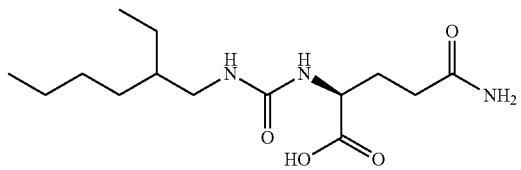 [SMILES: CCCCC(CC)CNC(=O)N[C@@H](CCC(N)=O)C(=O)O]

Was compared with compound II, which is an alternative substrate according to U.S. Pat. No. 5,925,339:

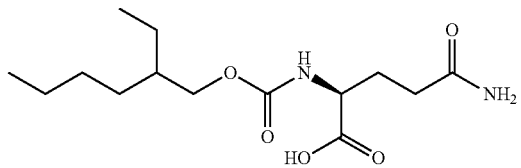 [SMILES: CCCCC(CC)COC(=O)N[C@@H](CCC(N)=O)C(=O)O]

TABLE 1

Inhibition of the release of 3-hydroxy-3-methyl-hexanoic acid

| | Preincubation time (h) | % inhibition by various concentration of test compound | | | |
| --- | --- | --- | --- | --- | --- |
| | | 10 ppm | 100 ppm | 500 ppm | 1000 ppm |
| Compound Ia | 0.5 h | 61.0 | 75.8 | 92.4 | 92.5 |
| Compound Ia | 4 h | 52.2 | 81.2 | 100.0 | 91.5 |
| Compound Ia | 8 h | 65.2 | 86.0 | 100.0 | 91.8 |
| Compound Ia | 24 h | 19.9 | 83.2 | 100.0 | 89.6 |
| Compound II | 0.5 h | 2.8 | 33.4 | 76.6 | 83.0 |
| Compound II | 4 h | -4.4 | -25.2 | 59.9 | 79.5 |
| Compound II | 8 h | 8.3 | -9.8 | -5.6 | 41.3 |
| Compound II | 24 h | -1.0 | -13.3 | -28.8 | -23.1 |

TABLE 2

Release of 2-ethyl-hexanol or 2-ethyl-hexylamine

|  | Preincubation time (h) | 10 ppm | 100 ppm | 500 ppm | 1000 ppm |
|---|---|---|---|---|---|
| Compound Ia | 0.5 h | b.d. | b.d. | b.d. | b.d. |
| Compound Ia | 4 h | b.d. | b.d. | b.d. | b.d. |
| Compound Ia | 8 h | b.d. | b.d. | b.d. | b.d. |
| Compound Ia | 24 h | b.d. | b.d. | b.d. | b.d. |
| Compound II | 0.5 h | 3.9 | 26.6 | 55.6 | 78.3 |
| Compound II | 4 h | 3.1 | 29.8 | 115.2 | 177.3 |
| Compound II | 8 h | 3.1 | 27.6 | 152.3 | 288.2 |
| Compound II | 24 h | 2.3 | 17.5 | 89.5 | 176.0 |

Note:
For compound Ia, release of 2-ethyl-hexylamine was assessed, and, correspondingly, for Compound II the release of 2-ethyl-hexanol was determined. b.d. = below detection limit. From 1000 pm of compound II, in theory a maximum of 430 ppm 2-ethyl-hexanol can be released, this maximum is not achieved as the bacteria further metabolise this compound.

The data in Table 2 show that Compound II is cleaved by the bacteria whereas compound Ia is stable. The amount of released 2-ethylhexanol progressively increases with time, and then starts to disappear at 24 h due to further bacterial metabolism.

The inhibition for molecule II as shown in Table 1 therefore is reduced upon prolonged preincubation. On the other hand, inhibition by compound Ia basically remains constant after prolonged preincubation with the bacteria. Thus Compound Ia is a true inhibitor, whereas Compound II is an alternative substrate. Inhibition values for compound II even become negative, indicating that the substrate stimulates production of the enzyme by the bacteria, which is not uncommon for bacteria (i.e. substrate-dependent activation of catabolic genes).

From the data in Table 1 IC50 values (Concentration for 50% inhibition of malodour release) can be estimated. These are shown in Table 3.

|  | IC 50 (in ppm) | |
|---|---|---|
| Preincubation time | compound Ia | compound II |
| 0.5 h | <10 | 253.3 |
| 4 h | <10 | 387.2 |
| 8 h | <10 | >1000 |
| 24 h | 52.8 | >>1000 |

Compound Ia has a surprisingly good inhibitory activity when compared to the alternative substrate compound II. Thus with 0.5 h preincubation time, compound Ia is >25 fold stronger as compound II and with 8 h preincubation time it is >100 times more active.

EXAMPLE 3

Inhibition of Formation of Malodorous Acids:
Comparison of Activity of Inventive Compound in Different Bacterial Species The inhibition of malodour release was tested on different bacterial species, all isolated from the human axilla. The method from Example 2 was used.

As indicated in Table 4, the inventive compound Ia is active in all bacterial species, indicating that it is efficiently transported into all of these bacteria, thus it gives a broad band activity

TABLE 4

% inhibition of release of 3-hydroxy-3-methyl-hexanoic acid in different bacterial species

|  | Pre-incubation. Time | Concen-tration (ppm) | % inhibition of release of 3-hydroxy-3-methyl-hexanoic acid | | | | | |
|---|---|---|---|---|---|---|---|---|
|  |  |  | Ax20 | Ax30 | Ax43 | Ax52 | Ax73 | Average |
| Ia | 0.5 h | 10 | 51 | 95 | 93 | 77 | 107 | 84.6 |
| Ia | 2 h | 10 | 50 | 93 | 97 | 86 | 70 | 79.2 |
| Ia | 0.5 h | 100 | 81 | 100 | 97 | 83 | 87 | 89.6 |
| Ia | 2 h | 100 | 86 | 100 | 99 | 94 | 94 | 94.6 |

Ax20 *Corynebacterium glaucum*;
Ax30, *Arthrobacter woluwensis*;
Ax43, *Corynebacterium tuberculostearicum*;
Ax52, *Corynebacterium mucifaciens*;
Ax73, *Corynebacterium coyleae*

EXAMPLE 4

Inhibition of Formation of Malodorous Acids:
Comparison of Inventive Compounds with Different Residue R1

Compounds of different R1 were tested with the method of example 2, results are in Table 5.

TABLE 5

% inhibition of release of 3-hydroxy-3-methyl-hexanoic acid by compounds with different R1

| R1 | % Inhibition of release of 3-hydroxy-3-methyl-hexanoic acid (100 ppm test compound) |
|---|---|
| 2-ethyl-hexyl | 79.8 |
| 3-benzylphenyl | 71.0 |
| 4-benzylphenyl | 70.5 |
| 4-pentylphenyl | 66.2 |
| naphtyl | 65.9 |
| 4-butylphenyl | 63.6 |
| benzyl | 61.0 |
| cyclooctyl | 60.2 |
| 4-ethylphenyl | 60.1 |
| 4-isopropylphenyl | 58.9 |
| 3-ethylphenyl | 57.5 |
| 5-phenyl-3- | 56.5 |

EXAMPLE 5

Combination of the Inventive Compound with Polyaminopropyl Biguanide Salts (Cosmocil CQ)

The inhibition of malodour release by Compound Ia combined with polyaminopropyl biguanide salts (Cosmocil CQ) was tested with the method from Example 2.

|  | Cosmocil CQ | | | |
|---|---|---|---|---|
|  | 0 ppm | 100 ppm | 200 ppm | 500 ppm |
| Compound Ia, 0 ppm | 0.0 | 11.3 | 33.1 | 64.1 |
| Compound Ia, 10 ppm | 61.0 | 58.8 | 75.6 | 85.2 |
| Compound Ia, 100 ppm | 75.8 | 85.9 | 95.6 | 100.0 |

The results indicate that the antibacterial deodorant ingredient Cosmocil CQ gives insufficient control of malodour control even if tested at 500 ppm, whereas this activity is clearly improved by combining it with the inventive compound Ia.

The invention claimed is:

1. A compound of formula (I)

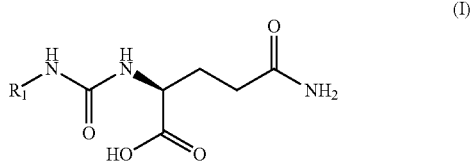

or salts thereof, wherein $R_1$ represents a group selected from the group consisting of 2-ethyl-hexyl, benzyl, 4-benzylphenyl, 3-benzylphenyl, 4-pentylphenyl, 4-butylphenyl, 4-propylphenyl, 4-isopropylphenyl, 4-ethylphenyl, 3-ethylphenyl, cyclooctyl and 5-phenyl-3-methyl-pentyl.

2. The compound according to claim 1 wherein $R_1$ represents a 2-ethyl-hexyl group.

3. The compound according to claim 1 wherein $R_1$ represents a benzyl group.

4. A composition comprising a compound according to formula (I)

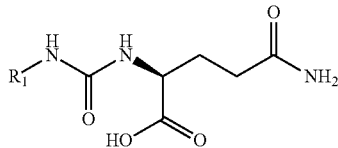

or salts thereof, wherein $R_1$ represents a group selected from the group consisting of 2-ethyl-hexyl, benzyl, 4-benzylphenyl, 3-benzylphenyl, 4-pentylphenyl, 4-butylphenyl, 4propylphenyl, 4-isopropylphenyl, 4-ethylphenyl, 3-ethylphenyl, naphthyl, cyclooctyl and 5-phenyl-3-methyl-pentyl.

5. The composition according to claim 4 wherein $R_1$ represents a 2-ethyl-hexyl group.

6. The composition according to claim 4 wherein $R_1$ represents a benzyl group.

7. The composition according to claim 4 wherein said compound is present in amounts of 0.05 to 2% by weight.

8. The composition according to claim 4 additionally comprising a polyaminopropyl biguanide salt.

9. The composition according to claim 4 that is a deodorant composition.

10. The composition according to claim 4 that is a product for treatment of fabrics.

11. A method of treating axillary malodour comprising applying to the human axilla a compound as defined in claim 1.

12. A method of treating axillary malodour comprising applying to the human axilla a composition as defined in claim 4.

* * * * *